United States Patent
Ryu

(10) Patent No.: US 7,348,463 B2
(45) Date of Patent: Mar. 25, 2008

(54) HYDROGENATION OF AROMATIC COMPOUNDS

(75) Inventor: J. Yong Ryu, League City, TX (US)

(73) Assignee: Catalytic Distillation Technologies, Pasadena, TX (US)

( * ) Notice: Subject to any disclaimer, the term of this patent is extended or adjusted under 35 U.S.C. 154(b) by 4 days.

(21) Appl. No.: 11/389,955

(22) Filed: Mar. 27, 2006

(65) Prior Publication Data

US 2007/0225531 A1  Sep. 27, 2007

(51) Int. Cl.
*C07C 13/465* (2006.01)
*C07C 5/10* (2006.01)

(52) U.S. Cl. ............................. 585/270; 585/266

(58) Field of Classification Search ........... 585/266, 585/270
See application file for complete search history.

(56) References Cited

U.S. PATENT DOCUMENTS

| 5,773,670 | A  | 6/1998 | Gildert et al. |
| 5,856,602 | A  | 1/1999 | Gildert et al. |
| 6,187,980 | B1 | 2/2001 | Gildert |
| 6,429,338 | B1 | 8/2002 | Burdeniuc et al. |
| 6,750,374 | B2 | 6/2004 | Sanderson et al. |
| 6,855,853 | B2 | 2/2005 | Groten et al. |
| 2005/0010070 | A1 | 1/2005 | Ryu |
| 2005/0033099 | A1 | 2/2005 | Ryu et al. |
| 2005/0209491 | A1 | 9/2005 | Ryu |

OTHER PUBLICATIONS

Notification of Transmittal of International Search Report and Written Opinion of the International Searching Authority, or the Declaration for Application No. PCT/US06/45173 mailed Oct. 15, 2007 (9 pages).

*Primary Examiner*—J. Parsa
(74) *Attorney, Agent, or Firm*—Osha Liang LLP

(57) ABSTRACT

A process for hydrogenating aromatic compounds to produce hydrogenated cyclic compound by contacting an aromatic compound with hydrogen under conditions of pressure and temperature to react the hydrogen and aromatic compound in the presence of a catalyst comprising from 4 to 14 wt. % Ni and 0.0 up to about 0.9 wt. % Cu deposited on a transition alumina support having BET surface area of from about 40 to 180 m2/g, and pore volume of from about 0.3 to about 0.8 cc/g, preferably in the presence of a solvent boiling at least 10° F. higher than the aromatic compound and the hydrogenated cyclic compound, such as the hydrogenation of benzene to produce cyclohexane.

9 Claims, No Drawings

HYDROGENATION OF AROMATIC COMPOUNDS

BACKGROUND OF THE INVENTION

1. Field of the Invention

The present invention relates to a process for hydrogenation of aromatic compounds such as the hydrogenation of benzene to cyclohexane and the supported nickel catalyst modified with up to 0.9 wt. % Cu therefor.

2. Related Information

Cyclohexane is the main precursor for the production of nylon products and as such, the demand remains strong. Cyclohexane was first obtained by the direct fractional distillation of suitable crude petroleum refinery streams. Now the major portion of cyclohexane is obtained from the direct hydrogenation of benzene. Conventionally the reaction is carried out in vapor or mixed phase using a fixed bed reaction. The reactor temperature is controlled to be between 350 to 500° F. Higher temperatures can lead to thermodynamic limitations on benzene conversion, thermal cracking and increased by-product. In general, the amount of byproducts in the effluent stream from a hydrogenation reactor increases with hydrogenation temperature or conversion of benzene or both.

Peterson in U.S. Pat. No. 2,373,501 discloses a liquid phase process for the hydrogenation of benzene to cyclohexane wherein a temperature differential is maintained between the top of the catalyst bed where benzene is fed and the outlet where substantially pure cyclohexane is withdrawn. The temperature differential is due to the change in the exothermic heat of reaction released as less and less benzene is converted as the concentration of benzene decreases. Specifically the top of the catalyst bed is at a higher temperature than the lower catalyst bed. Hydrogen is supplied countercurrent to the benzene/cyclohexane flow. Temperature control coils are disposed within the reactor to maintain the temperature differential if the exothermic heat of reaction is not sufficient or to cool the bed if too much heat is released. Peterson recognizes that although the bulk of his reaction takes place in the liquid phase a portion of the benzene and cyclohexane will be vaporized, especially near the top of the reactor where the benzene concentration is highest and conversion is highest. A reflux condenser is provided to condense the condensible material and return it to the reactor. Thus, a substantial portion of the heat of reaction is removed by condensation of the reactants vaporized throughout the reaction. Peterson maintains a liquid level above the topmost catalyst bed but allows room for vapors to escape to the condenser where the heat of reaction is removed.

Larkin, et al. in U.S. Pat. No. 5,189,233 disclose another liquid phase process for the hydrogenation of benzene to cyclohexane. However, Larkin, et al utilize high pressure (2500 psig) to maintain the reactants in the liquid state. In addition Larkin, et al disclose the use of progressively more active catalyst as the concentration of benzene decreases to control the temperature and unwanted side reactions.

Hui, et al. in U.S. Pat. No. 4,731,496 disclose a gas phase process for the hydrogenation of benzene to cyclohexane over a specific catalyst. The catalyst reported therein is nickel supported on a mixture of titanium dioxide and zirconium dioxide.

U.S. Pat. No. 6,750,374 discloses a process for the hydrogenation of benzene using hydrogen containing up to about 15 mole % impurities, such as carbon monoxide and light hydrocarbons with an alumina supported catalyst containing from about 15 to 35 wt. % Ni and from about 1 to 15 wt. % Cu. The catalyst may contain additional elements such as Mo, Zn, Co, Fe.

SUMMARY OF THE INVENTION

The present invention is a process and a catalyst used in the process for hydrogenation of aromatic compounds, such as benzene, aniline, naphthalene, phenol and benzene polycarboxylates, by hydrogenating the aromatic compound in the presence of a catalyst comprising from 4 to 14 wt. % Ni, preferably 9 to 10 wt. % Ni and up to about 0.9 wt. % Cu, preferably about 0.2 to 0.4 wt. % Cu deposited on a transition alumina support having BET surface area of from about 40 to 180 m2/g, and pore volume of from about 0.3 to about 0.8 cc/g. The hydrogenation of aromatic compounds is advantageously carried out in the presence of a high boiling solvent. The preferred solvent will have at least 10° F. higher boiling point than the aromatic compound to be hydrogenated and hydrogenated cyclic compound. The advantages of using a high boiling solvent are higher productivity of cyclohexane and keeping the temperature of catalytic reaction zone in a desired range. The high boiling solvent provides improvement in productivity of the reaction system whether or not the nickel catalyst is modified with copper.

In the production cyclohexane, benzene is present in the reaction stream in an amount of 1 to 60 wt. %, preferentially of 3 to 40 wt. %. The hydrogen stream may be pure hydrogen or may contain up to 5 mole % impurities including carbon monoxide. The remaining components in the reaction stream can be cyclohexane, a high boiling solvent or a mixture of cyclohexane and a high boiling solvent. If a high boiling solvent is used, the solvent may comprise 10 to 90 wt. %, preferably 20 to 80 wt % of the reaction stream. The high boiling solvent may be recovered from the effluent recycle stream and recycled to hydrogenation reactor. The content of cyclohexane in the recycle solvent stream can be 0.0 to 80 wt. %, preferably from 0.5 to 30 wt %.

The present invention also includes a copper modified nickel catalyst used in the hydrogenation of aromatic compound to produce a hydrogenated cyclic compound comprising 4 to 14 wt. % Ni and about 0.2 to 0.4 wt. % Cu deposited on a transition alumina support having BET surface area of from about 40 to 180 m2/g, and pore volume of from about 0.3 to about 0.8 cc/g.

DETAILED DESCRIPTION OF THE PREFERRED EMBODIMENT

This invention pertains to a catalytic hydrogenation process of aromatic compounds such as benzene, aniline, naphthalene and phenol in the presence of improved copper modified nickel-based catalyst supported on a porous support. Hydrogenation of benzene yields cyclohexane. But the hydrogenation product stream from the catalytic reactor contains other undesired by-products such as pentane, cyclopentane, methyl cyclopentane, n-hexane and methyl cyclohexane. The product stream usually contains a trace amount of benzene, up to about 200 ppm by weight. Less than 10 ppm benzene is highly desirable for the production of high purity cyclohexane. In general, the amount of by-products in the effluent stream from a hydrogenation reactor increases with hydrogenation temperature or conversion of benzene or both. Especially the amount of the by-products rapidly increases with hydrogenation temperature higher than about 340° F. The hydrogenation of aniline yields cyclohexylamine. But the undesired side reactions are deamination, formation of di and triphenylamine and various heavier products. An advantage of the present invention is reduced by-products so that simple distillation of hydrogenation product stream produces high purity cyclohexane product. Preferably the cyclohexane product contains no more than about 50 ppm, preferably no more 30 ppm by weight impurities including unconverted benzene excluding impurities came in with the feed benzene. The hydrogenation reactor effluent contains small amounts of cyclohexene. Since cyclohexene can easily be hydrogenated to cyclohexane by recycling the reactor effluent or using a small separate reactor without producing significant amounts of by-product, it is not considered as an undesired by-product. The present invention provides a significant improvement of the productivity of cyclohexane as well as reducing total impurities in the product cyclohexane stream from the catalytic reaction zone to less than 10 ppm, if the benzene hydrogenation is carried out in the presence of a heavy solvent such as decalin and decane. An additional advantage of using heavy solvent is substantially less recycle of hydrogen.

The hydrogenation reaction can be carried out in any physical device such as catalytic distillation column, fixed bed reactor, boiling point reactor, stirred tank reactor, trickle bed reactors or any combination of these. Since the benzene hydrogenation reaction is exothermic reaction, the hydrogenation reaction for the traditional fixed bed operation is preferably carried out by recycling the reactor effluent stream to dilute the fresh benzene feed, which dilutes the heat of reaction. Although recycling the reactor effluent is not necessary for the catalytic distillation reactor, one may choose to do so.

The present catalysts preferably comprise Ni and Cu and optionally one or more elements selected from the group consisting of Ag, Ru, Re, Zn, Mo and Pd which are deposited on a support comprising transitional aluminas such as crystalline alumina of gamma, kappa, delta, theta and alpha or a mixture comprised of two or three selected therefrom. A preferred nickel content of the catalyst is from about 9 to 10 wt. % and a preferred copper contents is from about 0.2 to 0.4 wt. %. The catalyst used in this invention is prepared by depositing nickel and copper on a porous support. Copper serves to improve the catalyst activity and selectivity. The catalyst may contain one or more elements as the second optional modifiers from Ag, Ru, Re, Zn, Mo, and Pd. The deposition of active metal components can be carried out by any technique such as incipient impregnation, spray coating impregnation. The preferred support will have average of size from about 0.5 mm to about 3 mm, preferably from about 1 mm to about 2.5 mm.

The transition alumina is obtained by calcining at about 850 to about 1200° C., and preferably having the following physical properties after calcining at from 850 to 1200° C.: BET surface of from about 40 to about 180 $m^2/g$, preferably from 50 to 120 $m^2/g$ and pore volume of from about 0.3 to about 0.8 cc/g. The transition alumina is the crystalline alumina of delta, theta, kappa or a mixture composed of two or three from gamma, kappa, delta, theta and alpha.

The physical shapes of the preferred aluminas in this invention can be any shape such as spheres, extrudates, pellets and granules which preferably have diameters of less than about ¼ inch, preferably ⅛ inch and less than about ½ inch length, and preferably less than ¼ inch length for extrudates or pellets.

Deposition of the nickel on a support can be carried out by single or multiple impregnations. A solution of the nickel compound is prepared by dissolving a nickel compound or an organo nickel compound in organic solvent or water. The examples of the nickel compounds are nickel salts such as nickel nitrate or organo metallic nickel compounds such as nickel acetate, nickel formate, nickel acetylacetonate and nickel alkoxides. The impregnation product is dried and calcined at temperature in a range from 200° to 600° C., preferably from 250° to 500° C.

When the hydrogenation of benzene is carried out in a fixed bed reactor, which is operated in boiling point mode, or in a catalytic distillation reactor, the heat of hydrogenation reaction is utilized to vaporize the product cyclohexane. The result of the vaporization is the internal cooling of the hydrogenation reaction zone. The overhead vapor stream from a catalytic distillation reactor, which is operated in the presence or absence of a high boiling solvent, comprises cyclohexane and hydrogen.

CONTROL EXAMPLE 1

A commercial 28 wt. % Ni catalyst (1.2 mm diameter trilobe extrudates) was tested to hydrogenate of benzene. The crystal form of alumina support of this catalyst is gamma-alumina. The physical properties of this catalyst were 113 $m^2/g$ BET, 0.43 cc/g total nitrogen pore volume and an average pore diameter of 15 nm. 50 grams of the catalyst was loaded in a vertically mounted up-flow stainless steel fixed bed reactor (1 inch diameter×20 inch long). Two thermocouples at each end of catalyst zone were installed to control the reactor temperature. The catalyst was supplied by the manufacturer as activated and passivated form, and recommended reactivation at 482° F. in hydrogen gas flow. The catalyst was reactivated at 250° F. in 300 cc/min gas flow of 33 volume % hydrogen gas in nitrogen for 1.5 hours and then 575° F. for 5 hours in 350 cc/min flow of pure hydrogen gas. The hydrogenation of benzene was carried out under various conditions. The results are listed in Table 1.

TABLE 1

| Temp ° F. | 300 | 320 | 340 | 340 | 350 | 360 |
|---|---|---|---|---|---|---|
| Press, psig | 250 | 250 | 250 | 250 | 250 | 250 |
| Benzene feed rate, ml/min | 6 | 6 | 11.2 | 6 | 6 | 6 |
| Benzene Conversion, % | 18.21 | 20.21 | 21.59 | 17.71 | 18.41 | 17.86 |
| Selectivity of cyclohexane and cyclohexene, m % | 99.95 | 99.87 | 99.91 | 99.84 | 99.84 | 99.82 |
| By-products per 100% cyclohexane and cyclohexene combined, wt. ppm | | | | | | |
| Cyclopentane | 439 | 1114 | 644 | 1296 | 1359 | 1520 |
| Methylcyclohexane | 0 | 0 | 7 | 0 | 0 | 0 |
| Hexane | 0 | 0 | 7 | 0 | 0 | 0 |
| Methyl cyclopentane | 692 | 1306 | 472 | 1546 | 1669 | 1881 |
| Sum of by-products | 1131 | 2420 | 1130 | 2842 | 3028 | 3401 |
| Cyclohexene | 854 | 165 | 1661 | 1201 | 1309 | 2056 |

EXAMPLE 2

A spherical gamma-alumina (1.68 mm diameter) support was calcined at 1100° C. for 3 hours. The alumina spheres prior to the calcination had 145 m$^2$/g BET surface area, a total nitrogen volume of 0.925 cc/g and an average pore diameter of 21.6 nm. After calcination, the diameter of alumina spheres was changed to 1.45 mm, which had 56 m$^2$/g BET, a total nitrogen pore volume of 0.701 cc/g and an average pore diameter of 36.2 nm. Its x-ray diffraction indicated mostly theta-alumina with minor amount of delta.

A mixed solution of nickel nitrate and copper nitrate was prepared by dissolving 86.5 grams of Ni(NO$_3$)$_2$.2.5H$_2$O in 25.95 grams of water. 300 grams of the calcined alumina was placed in a rotary impregnator. The mixed solution was sprayed on rolling alumina spheres inside the rotary impregnator by using a liquid sprayer over a period of about 15 minutes. The content in the rotary impregnator was dried by blowing hot air in at about 200° C. The dried product was calcined at 350° C. for 2 hours.

The second mixed solution was prepared by dissolving 65 grams of Ni(NO$_3$)$_2$.6H$_2$O and 1.8 grams of Cu(NO$_3$)$_2$.2.5H$_2$O in 19.5 grams of water. The second impregnation was performed on the first impregnation product in similar manner to the first impregnation. The dried impregnation product was calcined at 380° C. for 2 hours.

Based on the amount of materials used, the finished catalyst would contain 9.22 wt % Ni and 0.35 wt. % Cu. The examination of the catalyst spheres under microscope indicated that the active metal components were deposited in an outer layer of spheres. The average layer thickness was about 0.33 mm. The physical properties of this catalyst were 60 m$^2$/g, 0.56 cc/g total nitrogen pore volume and an average pore diameter of 39 nm. 50 grams of this catalyst was loaded in the same reactor used in the Control Example 1. The catalyst was activated at 250° F. in 300 cc/min gas flow of 33 volume % hydrogen gas in nitrogen for 1.5 hours and then for 3 hours at each 670 and 770° F. by passing 350 cc/min of pure hydrogen gas. The hydrogenation of benzene was carried out under various conditions. The results are listed in Table 2. As shown in Table 2, the hydrogenation reaction product streams from the reactor do not contain any detectable amounts of by-products. The performance of this catalyst is superior to the conventional nickel catalysts.

TABLE 2

| Temp ° F. | 300 | 320 | 320 | 340 | 340 | 350 | 360 |
|---|---|---|---|---|---|---|---|
| Press, psig | 250 | 250 | 250 | 250 | 250 | 250 | 250 |
| Benzene feed rate, ml/min | 6 | 6 | 11.2 | 11.2 | 6 | 6 | 6 |
| Benzene Conversion, % | 24.45 | 18.69 | 28.28 | 21.48 | 25.59 | 14.34 | 19.44 |
| Selectivity of cyclohexane and cyclohexene, m % | 100 | 100 | 100 | 100 | 100 | 100 | 100 |
| By-products in product stream based on 100% cyclohexane and cyclohexene combined, wt. ppm | | | | | | | |
| Cyclopentane | 0 | 0 | 0 | 0 | 0 | 0 | 0 |
| Methylcyclohexane | 0 | 0 | 0 | 0 | 0 | 0 | 0 |
| Hexane | 0 | 0 | 0 | 0 | 0 | 0 | 0 |
| Methyl cyclopentane | 0 | 0 | 0 | 0 | 0 | 0 | 0 |
| Sum of by-products | 0 | 0 | 0 | 0 | 0 | 0 | 0 |
| Cyclohexene | 1613 | 4734 | 1285 | 2088 | 1549 | 3115 | 2235 |

EXAMPLE 3

A nickel catalyst was prepared according to US Publication No. 2005-0033099-A1. Gamma-Alumina (1.3 mm diameter trilobe extrudates) was calcined at about 1000° C. for 3 hours in air. The gamma-alumina had 252 m$^2$/g BET, a total nitrogen pore volume of 0.571 cc/g and an average pore diameter of 8.85 nm. A solution of nickel nitrate was prepared by dissolving 183.6 g Ni(NO$_3$)$_2$.6H$_2$O in 295 grams water. 300 g of the calcined alumina support was placed in a rotary impregnator and then the nickel nitrate solution was poured on tumbling alumina extrudates in the rotary impregnator. After 15 minutes cold roll, the content in the rotary impregnator was dried at about 200° C. by blowing hot air into the rotary drier. The dried product was calcined at 380° C. for 2 hours. Based on the amount of nickel nitrate used to prepare this catalyst, the finished catalyst would have 11 wt % Ni on alumina support. Measurement of the physical properties of the finished catalyst indicated 133 m$^2$/g BET surface area, a total nitrogen pore volume of 0.622 cc/g and an average pore diameter of 18.6 nm.

50 grams of this catalyst was loaded in the same reactor used in the Control Example 1. The catalyst was activated in identical manner to the Example 2. The hydrogenation of benzene was carried out under various conditions. The results are listed in Table 3. Comparing the performance data of this catalyst in Table 3 with those in the Table 1 of the Control Example 1 indicates a superior performance of this catalyst to conventional nickel catalysts, although it was not as good as the catalyst in the Example 2.

experiment demonstrates hydrogenation of mixed feed stream to hydrogenation, where the mixed feed represents a stream obtained by mixing 1 weight portion of fresh benzene with 3 weight portion of the reactor effluent recycle steam.

The same catalyst (50 grams) in the Example 2 was in the same reactor used in the Control Example 1. The catalyst was activated in same manner to the Example 2. A feed mixture of benzene and cyclohexane was prepared. The composition of the feed was 0.11 wt % lights, 25.41 wt % benzene and 74.48 wt % cyclohexane. The hydrogenation of benzene was carried out under various conditions. The impurities in the feed and product streams were analyzed with a trace go analysis method. The result is listed in Table 4. The impurities in product streams mostly originated from impurities in the feed. All combined, the total amount of various impurities (listed in Table 4) produced during the hydrogenation of benzene according to this invention is less than 10 ppm. The conversion of benzene could be forced so high that the benzene contents in the reactor effluent streams could be reduced to less than 35 ppm by weight. This example demonstrates that it is possible to obtain extremely

TABLE 3

| Temp ° F. | 300 | 320 | 340 | 340 | 350 | 360 |
|---|---|---|---|---|---|---|
| Press, psig | 250 | 250 | 250 | 250 | 250 | 250 |
| Benzene feed rate, ml/min | 6 | 6 | 11.2 | 6 | 6 | 6 |
| Benzene Conversion, % | 18.92 | 28.28 | 21.48 | 25.59 | 14.34 | 19.44 |
| Selectivity of cyclohexane and cyclohexene, m % | 100.00 | 100.00 | 99.97 | 99.94 | 99.95 | 99.97 |
| By-products in product stream based on 100% cyclohexane and cyclohexene combined, wt. ppm | | | | | | |
| Cyclopentane | 0 | 0 | 225 | 493 | 386 | 273 |
| Methylcyclohexane | 0 | 0 | 0 | 0 | 0 | 0 |
| Hexane | 0 | 0 | 0 | 0 | 0 | 0 |
| Methyl cyclopentane | 0 | 0 | 0 | 0 | 0 | 0 |
| Sum of by-products | 0 | 0 | 225 | 493 | 386 | 273 |
| Cyclohexene | 555 | 846 | 890 | 565 | 765 | 1846 |

EXAMPLE 4

This example demonstrates the hydrogenation of benzene with recycle of reactor effluent in the absence of a heavy solvent. But the feed to the reactor comprises fresh benzene feed and reactor effluent stream, which is cyclohexane. This high conversion (>99.99%) of benzene with a cyclohexane selectivity equivalent to about 99.999 mole %. The productivity of cyclohexane at two conditions of the two right columns in Table 4 were 29.2 and 31.8 m/fur per kg catalyst. This is a demonstration of superior catalyst performance compared to the prior art represented by Example 1.

TABLE 4

| | | | | | | | |
|---|---|---|---|---|---|---|---|
| Temp-in, ° F. | | 144 | 158 | 145 | 160 | 159 | 160 |
| Temp-out, ° F. | | 299 | 329 | 310 | 300 | 322 | 322 |
| Press, psig | | 230 | 230 | 230 | 230 | 230 | 230 |
| H2 Rate, cc/min | | 155 | 185 | 287.5 | 340 | 500 | 500 |
| Flow rate of feed sole, ml/min | | 6 | 6 | 11.2 | 11. | 29.6 | 10.5 |
| WHSV, hr$^{-1}$ | | 5.8 | 5.8 | 10.8 | 10.8 | 9.2 | 10.1 |
| Benzene Conversion, % | | 77.26 | 99.81 | 74.21 | 83.26 | 100 | 99.99 |
| Productivity of cyclohexane (m/hr/kg) | | | | | | 29.2 | 31.8 |
| Trace analysis (wt ppm) | Feed | | | | | | |
| Isopentane | 1.7 | 1.2 | 1.9 | 0.9 | 1.0 | 1.8 | 1.9 |
| Methylpentane | 12.5 | 12.0 | 14.3 | 12.7 | 13.1 | 10.9 | 10.9 |
| Pentane | 1.3 | 1.9 | 1.6 | 1.6 | 1.8 | 1.7 | 1.8 |
| Cyclopentane | 5.9 | 8.1 | 6.4 | 7.2 | 7.4 | 5.8 | 5.9 |
| Hexane | 13.5 | 13.3 | 15.3 | 13.9 | 14.0 | 12.4 | 12.5 |
| Methyl cyclopentane | 11.1 | 12.4 | 13.1 | 12.1 | 12.2 | 10.8 | 10.9 |
| Benzene | | 5.78* | 0.05* | 6.59* | 4.27* | 9.9 | 34.2 |
| Cyclohexane | — | — | — | — | — | — | — |
| Cyclohexene | 4.7 | 14.8 | 5.5 | 24.9 | 4.8 | 4.5 | 0 |

TABLE 4-continued

| Methyl cyclohexane | 7.2 | 8.9 | 7.6 | 8.7 | 9.4 | 9.3 | 9.4 |
|---|---|---|---|---|---|---|---|
| Toluene | 3.1 | 3.2 | 3.2 | 2.3 | 1.7 | 0 | 0 |

*Weight %

EXAMPLE 5

This example demonstrates the hydrogenation of benzene in the presence of decalin as high boiling solvent, where the conversions of benzene to cyclohexane are close to 100%.

50 grams of the catalyst prepared in the Example 2 was loaded in the same reactor used in the Control Example 1. The catalyst was activated in same manner to the Example 2. The feed was a mixture of 0.44 wt % lights, 25.26 wt % benzene and 74.30 wt % decalin. The average total combined impurities in the feed, which boil at temperatures near to cyclohexane, was about 14.8 ppm. The hydrogenation of benzene was carried out under various conditions. The impurities in the feeds and product streams were analyzed with a regular gc analysis method and a trace gc analysis method. The results are listed in Table 5. The impurities in products under various conditions were mostly originated from impurities in feed. All combined, the total amount of various impurities produced during the hydrogenation of benzene according to this invention is less than 4 ppm by weight based on 100% cyclohexane. The trace amount of benzene in product stream can be reduced to less than 2 ppm in the product cyclohexane by adjusting the flow rate of hydrogen to the hydrogenation reactor at a given feed rate of benzene.

Surprisingly no trace amount of cyclohexene in any product stream was found. The productivity of cyclohexane was at least 40% higher than carrying out hydrogenation in the absence of a high boiling solvent in Example 4.

TABLE 5

| Temp-in, °F. | 218 | 220 | 219 | 220 |
|---|---|---|---|---|
| Temp-out, °F. | 322 | 330 | 328 | 333 |
| Press, psig | 230 | 230 | 230 | 230 |
| H2 Rate, cc/min | 400 | 430 | 385 | 405 |
| Flow rate of feed sole, ml/min | 15 | 15 | 13 | 13 |
| WHSV, hr$^{-1}$ | 16 | 16 | 13.9 | 13.9 |
| Benzene Conversion, % | 100 | 100 | 100 | 100 |
| Productivity of cyclohexane (m/hr/kg) | 50.9 | 50.9 | 44.2 | 44.3 |
| Trace analysis (wt ppm) | Feed | | | |
| Isopentane | 1.0 | 1.4 | 1.2 | 1.6 | 0.3 |
| Pentane | 1 | 0.3 | 0.3 | 0.3 | 0.3 |
| Cyclopentane | 0 | 0.6 | 0.4 | 0.3 | 0.3 |
| Hexane | 5.0 | 0.4 | 0.3 | 1.3 | 1.3 |
| Methyl cyclopentane | 1.1 | 0.6 | 0.4 | 0.4 | 0.4 |
| Benzene | — | 14.9 | 5.1 | 0.3 | 0.3 |
| Cyclohexane | — | — | — | — | — |
| Cyclohexene | 0.2 | 0 | 0 | 0 | 0 |
| Methyl cyclohexane | 4.7 | 7.0 | 6.7 | 6.7 | 6.5 |
| Toluene | 2.1 | 0 | 0 | 0 | 0 |

EXAMPLE 6

This example demonstrates the hydrogenation of benzene in the presence of decane as high boiling solvent. The conversions of benzene were so high that the benzene contents in the product steams were close to undetectable.

50 grams of the catalyst prepared in the Example 2 was loaded in the same reactor used in the Control Example 1. The catalyst was activated in same manner to the Example 2. The feed was a mixture of 0.10 wt % lights, 30.26 wt % benzene and 69.64 wt % decane. The average total combined impurities (excluding benzene) in the feed, which boil at temperatures near to cyclohexane, was about 5.77 ppm. The hydrogenation of benzene was carried out under various conditions. The impurities in the feeds and product streams were analyzed with a regular gc analysis method and a trace gc analysis method. The result is listed in Table 6. The impurities in products under various conditions mostly originated from impurities in the feed. All combined, the total amount of various impurities produced during the hydrogenation of benzene according to this invention is about 11 ppm based on 100% cyclohexane. The productivity of cyclohexane was equivalent or better than the case of performing the hydrogenation in the absence of a high boiling solvent in Example 4.

TABLE 6

| Temp-in, °F. | 165 | 165 | 164 |
|---|---|---|---|
| Temp-out, °F. | 335 | 327 | 334 |
| Press, psig | 230 | 230 | 230 |
| H2 Rate, cc/min | 400 | 400 | 450 |
| Flow rate of feed sole, ml/min | 9 | 8.5 | 10 |
| WHSV, hr$^{-1}$ | 9.6 | 8 | 11 |
| Benzene Conversion, % | 100 | 100 | 100 |
| Productivity of cyclohexane (m/hr/kg) | 36.4 | 32.6 | 40.5 |
| Trace analysis (wt ppm) | Feed | | | |
| Isopentane | 0.2 | 0.2 | 0.3 | 0.2 |
| Cyclopentane | 0.1 | 0.9 | 1.0 | 0.9 |
| Methyl pentane | <0.1 | 0.1 | 0.2 | <0.1 |
| Hexane | 0.2 | 0.9 | 1.0 | 0.5 |
| Methyl cyclopentane | 1.7 | 2.4 | 2.4 | 2.0 |
| Benzene | — | 0.02 | <0.01 | 0.02 |
| Cyclohexane | 2.5 | — | — | — |
| Cyclohexene | <0.1 | 1.4 | 1.3 | 0 |
| Methyl cyclohexane | 2.3 | 4.6 | 4.4 | 4.5 |
| Toluene | 1.7 | 0 | 0 | 0 |

The invention claimed is:

1. A process for hydrogenating aromatic compounds in a reaction stream comprising contacting said reaction stream with hydrogen under conditions of pressure and temperature to react the hydrogen and aromatic compounds in the presence of a catalyst comprising from 4 to 10 wt. % Ni and 0.2 up to about 0.9 wt. % Cu deposited on a transition alumina support having BET surface area of from about 40 to 180 m$^2$/g, and pore volume of from about 0.3 to about 0.8 cc/g to produce a hydrogenated cyclic compound, wherein the catalyst contains one or more modifiers selected from the group consisting of Ag, Ru, Re and Pd.

2. The process according to claim 1 wherein the Cu content is about 0.2 to 0.4 wt. %.

3. The process according to claim 2 wherein the Ni content of the catalyst is about 9 to 10 wt %.

4. The process according to claim 1 wherein benzene is present in the reaction stream in an amount of 1 to 60 wt. % and the hydrogenated cyclic compound comprises cyclohexane.

5. The process according to claim 1 carried out in the presence of a solvent having a boiling point at least 10° F. higher than the aromatic compound to be hydrogenated and the hydrogenated cyclic compound.

6. The process according to claim 5 wherein the Cu content is about 0.2 to 0.4 wt. %.

7. The process according to claim 6 wherein the Ni content of the catalyst is about 9 to 10 wt %.

8. The process according to claim 5 wherein benzene is present in the reaction stream in an amount of 1 to 60 wt. % and the hydrogenated cyclic compound comprises cyclohexane.

9. The process according to claim 5 wherein the solvent comprises 10 to 90 wt. % of the reaction stream.

* * * * *